United States Patent
Allolio et al.

(10) Patent No.: US 9,814,789 B2
(45) Date of Patent: Nov. 14, 2017

(54) RADIOPHARMACEUTICAL PRODUCTS FOR DIAGNOSIS AND THERAPY OF ADRENAL CARCINOMA

(71) Applicants: JULIUS-MAXIMILIANS-UNIVERSITÄT WÜRZBURG, Würzburg (DE); Bruno Allolio, Würzburg (DE); Andreas Schirbel, Gelsenkirchen (DE); Stefanie Hahner, Würzburg (DE)

(72) Inventors: Bruno Allolio, Würzburg (DE); Andreas Schirbel, Gelsenkirchen (DE); Stefanie Hahner, Würzburg (DE)

(73) Assignee: Julius-Maximilians-Universität Würzburg, Würzburg (DE)

( * ) Notice: Subject to any disclaimer, the term of this patent is extended or adjusted under 35 U.S.C. 154(b) by 0 days.

(21) Appl. No.: 14/649,516

(22) PCT Filed: Sep. 26, 2013

(86) PCT No.: PCT/EP2013/002887
§ 371 (c)(1),
(2) Date: Jun. 3, 2015

(87) PCT Pub. No.: WO2014/048568
PCT Pub. Date: Apr. 3, 2014

(65) Prior Publication Data
US 2015/0328341 A1    Nov. 19, 2015

(30) Foreign Application Priority Data

Sep. 27, 2012 (EP) .................... 12006734

(51) Int. Cl.
*A61K 31/4178* (2006.01)
*A61K 31/4164* (2006.01)
*A61K 49/00* (2006.01)
*A61K 51/04* (2006.01)

(52) U.S. Cl.
CPC ...... *A61K 49/0052* (2013.01); *A61K 51/0453* (2013.01)

(58) Field of Classification Search
CPC ............ A61K 31/4164; A61K 31/4178; A61K 49/0052
USPC ........................ 514/396, 397, 400
See application file for complete search history.

(56) References Cited

U.S. PATENT DOCUMENTS

2005/0033060 A1    2/2005 Zolle et al.

OTHER PUBLICATIONS

Atucha et et al., "Structure-activity relationship of etomidate derivatives at the GABA$_A$ receptor: Comparison with binding to 11β-hydroxylase" *Bioorganic & Medicinal Chemistry Letters* (2009) 19(15):4284-4287.
Hahner et al., "[$^{123}$I]Iodometomidate for Molecular Imaging of Adrenocortical Cytochrome P450 Family 11B Enzymes" *Journal of Clinical Endocrinology & Metabolism* (2008) 93(6):2358-2365.
Hahner S et al., "[$^{131}$I]Iodometomidate for Targeted Radionuclide Therapy of Advanced Adrenocortical Carcinoma" *Journal of Clinical Endocrinology and Metabolism* (2012) 97(3):914-922.
Zolle et al., "New Selective Inhibitors of Steroid 11β-Hydroxylation in the Adrenal Cortex, Synthesis and Structure-Activity Relationship of Potent Etomidate Analogues" *Journal of Medical Chemistry* (2008) 54(7): 2244-2253.
International Search Report dated Feb. 11, 2014 for PCT Application No. PCT/EP2013/002887, filed Sep. 26, 2013.

*Primary Examiner* — Matthew Coughlin
*Assistant Examiner* — Sagar Patel
(74) *Attorney, Agent, or Firm* — Knobbe, Martens, Olson & Bear, LLP

(57) ABSTRACT

A radiopharmaceutical composition is disclosed comprising novel iodometomidate derivatives of formula (I) which bind specifically to adrenal enzymes and which exhibit an improved stability. The compounds of formula (I) are suitable for use in a diagnostic imaging method, e.g. for diagnosis of adrenocortical carcinoma. The compounds of formula (I) are further suitable for use in the treatment of adrenocortical carcinoma, by means of radionuclide therapy.

14 Claims, 9 Drawing Sheets

Figure 9

| Biodistribution | % ID/g | | | | factor | |
|---|---|---|---|---|---|---|
| | 15 min | 30 min | 120 min | 240 min | 15 Min./15 Min. IMTO | 240 Min./240 Min. IMTO |
| Iodometomidate | 491 | 321 | 93 | 27 | 1 | 1 |
| Azetidinylamide | 582 | 544 | 324 | 275 | 1.2 | 10 |
| Pyrrolidinylamide | 385 | 363 | 152 | 66 | 0.8 | 2.4 |
| Ethylmethylamide | 538 | 394 | 97 | 62 | 1.1 | 2.3 |

RADIOPHARMACEUTICAL PRODUCTS FOR DIAGNOSIS AND THERAPY OF ADRENAL CARCINOMA

BACKGROUND OF THE INVENTION

Due to advances in conventional imaging, adrenal masses are detected with increasing frequency. The prevalence of incidentalomas, i.e. tumors found by coincidence without clinical symptoms or suspicion, is increasing with age.

Adrenal masses represent a wide range of different pathological entities, e.g. adrenal adenomas as prevalent form, adrenocortical carcinomas, hyperplasias, pheochromocytomas, ganglioneuromas, renal angiomyolipomas, lipomas, lymphangiomas, metastases as well as misinterpreted retroperitoneal neoplasias such as sarcomas or renal cell carcinomas. Accordingly, the different lesions require highly variable therapies ranging from immediate surgery to observational follow-up. Having a finding in the adrenal gland on diagnostic imaging, the clinician faces the challenge to decide whether the lesion is harmful and what therapy has to be chosen.

A particular challenge is the distinction whether the adrenal mass is of adrenocortical origin. About 80% of all adrenal masses do not show any endocrine activity which renders laboratory diagnostics difficult. A particular problem is the diagnosis of adrenocortical carcinomas. Adrenocortical carcinoma (ACC) is a rare and highly malignant tumor associated with a bad prognosis for the patient. The 5-year overall survival rate for patients with ACC is about 40% and the median survival in patients with advanced disease (stage IV) is <1 year. In addition, one third of the patients are under the age of 30 years.

Conventional imaging provides only limited information about the origin of an adrenal lesion. Although both computerized tomography (CT) and magnetic resonance imaging (MRI) contribute significantly to the characterization of adrenal masses, they often fail to differentiate lesions with low fat content. In many cases neither CT nor MRI provide a clear diagnosis of an adrenal tumor.

A tumor biopsy may be needed to definitely characterize the origin of the tumor. However, in adrenocortical cancer this invasive procedure has been associated with a variety of adverse events. In particular, the risk for dissemination of tumor cells is very high leading to metastasis along the puncture channel.

Thus, noninvasive tools to characterize the tissue specificity of an adrenal lesion, in particular imaging tools for the diagnosis of adrenal masses, are of considerable interest. Furthermore, there is a need for an imaging method for monitoring and assessment of a cytotoxic therapy of adrenocortical carcinomas.

The presently available norcholesterol scintigraphy with [$^{131}$I]iodomethyl norcholesterol (NP59) and [$^{75}$Se]selenomethyl norcholesterol (Scintadren) is able to differentiate adrenal adenomas from other adrenal masses. However, the approach is time consuming and leads to a considerable patient radiation dose. Moreover, this technique is limited by poor spatial resolution and low specificity, because adrenal cancers may show highly variable uptake.

Recently, high-affinity binding of metomidate (MTO) to adrenal steroidogenic enzymes has led to its use as a radiotracer for adrenal steroidogenic tissue. Accordingly, [$^{11}$C]MTO has been introduced as a tracer for positron emission tomography (PET), differentiating adrenocortical from nonadrenocortical tissue with high specificity. However, due to the short half-life of $^{11}$C of about 20 min, use of [$^{11}$C]MTO-PET is restricted to PET centers with an on-site cyclotron. Moreover, the short half-life also limits its use to the early uptake of the tracer potentially missing the optimal target to background ratio. Therefore, more long-lived radionuclides and a better general availability of radiotracers for adrenocortical imaging are prerequisites for their successful use.

Hahner at al. (J. Clin. Endocrinol. Metab. June 2008, 93(6):2358-2365) have recently shown that iodometomidate (IMTO) binds to adrenal membranes with high affinity in vitro. Further, they have developed an in vivo detection system of adrenal enzymes 11β hydroxylase (Cyp11B1) and aldosterone synthase (CYP11B2) by [$^{123}$I]IMTO scintigraphy both in animals and humans. Since these enzymes are located exclusively in adrenocortical tissue, the findings of Hahner et al. suggest that [$^{123}$I]iodometomidate is a highly specific radiotracer for imaging of adrenocortical tissue.

In ACC, many patients have progressive disease despite standard treatment, indicating a need for new treatment options. Complete removal of the tumor is currently the best treatment option. But more than 80% of the patients receiving surgery with complete removal of the tumor develop a local recurrence and/or distant metastases. The only specific drug currently approved for the treatment of ACC is mitotane, which prolongs recurrence-free survival in an adjuvant setting. However, in advanced disease, it has an overall response rate of only 26% according to retrospective analyses. The combination of mitotane with etoposide, doxorubicin, cisplatin or streptozotocin is considered as current first-line therapy in metastatic ACC. However, response rates are low (25-50%). Accordingly, in many patients, salvage therapies are needed. So far, studies investigating targeted therapies in this patient population have been rather disappointing.

Recently it has been found that [$^{131}$I]iodometomidate not only binds to Cyp11B1 and CYP11B2 with high specificity and affinity, but also high tracer uptake was observed in both primary tumor and metastases in patients with ACC. The therapeutic activity of [$^{131}$I]IMTO radionuclide therapy has recently been assessed in patients with advanced ACC (Hahner et al, J. Clin. Endocrinol. Metab. March 2012, 97(3):914-922).

However, the biological half-life of IMTO in the blood of patients has been found to be very limited. Already after few minutes iodometomidate acid could be identified as a product of enzymatic hydrolysis. FIG. 1 shows the kinetics of metabolization of IMTO. In contrast to IMTO, iodometomidate acid has little or no affinity to the adrenal enzymes Cyp11B1 and CYP11B2, and it is released via the renal system.

Thus, there is a need for improved radiotracer compounds for diagnosis and treatment of adrenal masses, in particular adrenocortical carcinoma, which overcome the above-described shortcomings of the state of the art.

SUMMARY OF THE INVENTION

According to the present invention a radiopharmaceutical composition is provided comprising radioactively labeled iodometomidate derivatives having the formula (I):

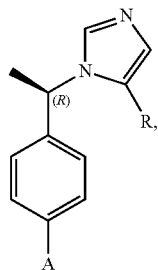

wherein A is a radioactive halogen selected from the group consisting of $^{123}$I, $^{124}$I, $^{125}$I and $^{131}$I;
R represents

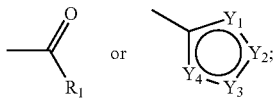

wherein $R_1$ represents

wherein each of $R_2$ and $R_3$ is independently selected from the group consisting of hydrogen and a linear or branched $C_1$-$C_4$ alkyl, optionally substituted with one or more substituents independently selected from OH, F, Cl, I and Br;
or $R_2$ and $R_3$ together form a 4-6-membered ring, optionally containing from 1 to 4 heteroatoms, selected from the group consisting of O, S, and N, optionally substituted with one or more substituents independently selected from OH, F, Cl, I and Br, a linear or branched $C_1$-$C_4$ alkyl, optionally substituted with one or more substituents independently selected from OH, F, Cl, I and Br;
each of $Y_1$, $Y_2$, $Y_3$ and $Y_4$ is independently selected from C, N, O and S;
and $Y_2$, and $Y_4$ are optionally substituted with a residue $R_4$ independently selected from the group consisting of hydrogen and a linear or branched $C_1$-$C_4$ alkyl, optionally substituted one or more substituents independently selected from OH, F, Cl, I and Br;
with the proviso that $R_1$ is not pyrrolidine;
or a pharmaceutically acceptable salt thereof, or solvate thereof.

In one aspect, the pharmaceutical composition is suitable for a diagnostic method, e.g. for diagnosis of adrenal tumors. When the compound is intended for use in a diagnostic method, A represents preferably $^{123}$I.

In another aspect, the pharmaceutical composition of the invention is suitable for the treatment of cancer, e.g. adrenocortical carcinoma, by means of internal radiotherapy. When the compound is intended for use in a treatment method, A represents preferably $^{131}$I.

The present invention also provides a compound of formula (I) as defined above.

Furthermore, the present invention includes a method for the preparation of a pharmaceutical composition comprising a compound of formula (I).

DESCRIPTION OF THE INVENTION

The present invention relates to a radiopharmaceutical composition comprising a compound having formula (I):

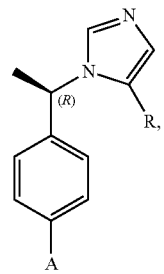

wherein
A is a radioactive halogen selected from the group consisting of $^{123}$I, $^{124}$I, $^{125}$I and $^{131}$I;
R represents

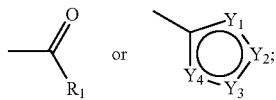

wherein $R_1$ represents

wherein each of $R_2$ and $R_3$ is independently selected from the group consisting of hydrogen and a linear or branched $C_1$-$C_4$ alkyl, optionally substituted with one or more substituents independently selected from OH, F, Cl, I and Br;
or $R_2$ and $R_3$ together form a 4-6-membered ring, optionally containing from 1 to 4 heteroatoms, selected from the group consisting of O, S, and N, optionally substituted with one or more substituents independently selected from OH, F, Cl, I and Br, a linear or branched $C_1$-$C_4$ alkyl, optionally substituted with one or more substituents independently selected from OH, F, Cl, I and Br;
each of $Y_1$, $Y_2$, $Y_3$ and $Y_4$ is independently selected from C, N, O and S,
and $Y_2$, and $Y_4$ are optionally substituted with a residue $R_4$ independently selected from the group consisting of hydrogen and a linear or branched $C_1$-$C_4$ alkyl, optionally substituted with one or more substituents independently selected from OH, F, Cl, I and Br;
with the proviso that $R_1$ is not pyrrolidine;
or a pharmaceutically acceptable salt thereof, or solvate thereof.

The compound having formula (I) comprises as residue A radioactive halogen. The radioactive halogen is preferably an iodine isotope, particularly $^{123}$I, $^{124}$I, $^{125}$I or $^{131}$I. More preferably, the iodine isotope is $^{123}$I (iodine-123) or $^{131}$I (iodine-131).

In one embodiment of the invention, A represents $^{123}$I. In this embodiment, the compounds of the invention are preferably suitable for use in a diagnostic method.

In another embodiment of the invention, A represents $^{131}$I. In this embodiment, the compounds of the invention are preferably suitable for use in a treatment method.

In a first aspect of the invention, residue R in formula (I) represents

wherein R$_1$ represents

wherein each of R$_2$ and R$_3$ is independently selected from the group consisting of hydrogen and a linear or branched C$_1$-C$_4$ alkyl, optionally substituted with one or more substituents independently selected from OH, F, Cl, I and Br, preferably F; or R$_2$ and R$_3$ together form a 4-6-membered ring, optionally containing from 1 to 4 heteroatoms, selected from the group consisting of O, S, and N, optionally substituted with one or more substituents independently selected from OH, F, Cl, I and Br, a linear or branched C$_1$-C$_4$ alkyl, optionally substituted with one or more substituents independently selected from OH, F, Cl, I and Br;

with the proviso that R$_1$ is not pyrrolidine.

Preferably, R$_1$ is selected from the group consisting of NH2,

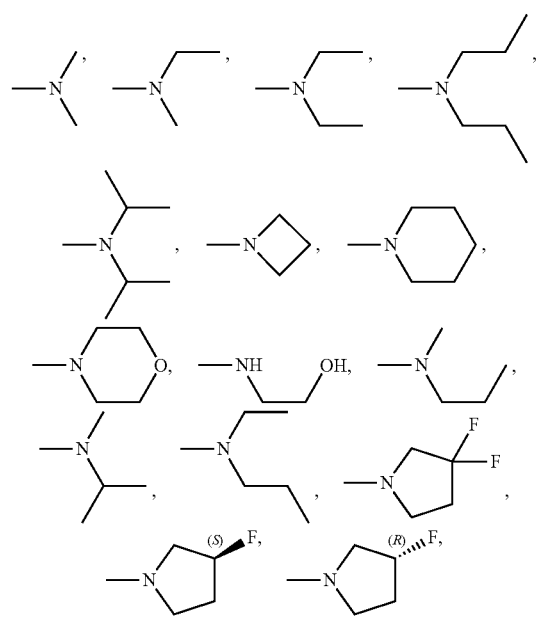

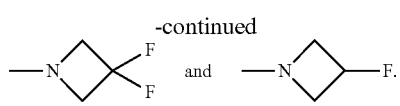

In one embodiment, R$_1$ represents

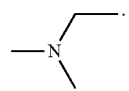

In one embodiment, R$_1$ represents

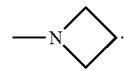

In a second aspect of the invention residue R in formula (I) represents

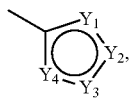

wherein each of Y$_1$, Y$_2$, Y$_3$ and Y$_4$ is independently selected from C, N, O and S, wherein Y$_2$, and Y$_4$ are optionally substituted with a residue R$_4$ independently selected from the group consisting of hydrogen and a linear or branched C$_1$-C$_4$ alkyl, optionally substituted with one or more substituents independently selected from OH, F, Cl, I and Br.

In a preferred embodiment, Y$_2$, and/or Y$_4$ is substituted by a residue R$_4$ independently selected from the group consisting of methyl, ethyl, isopropyl, tert-butyl,

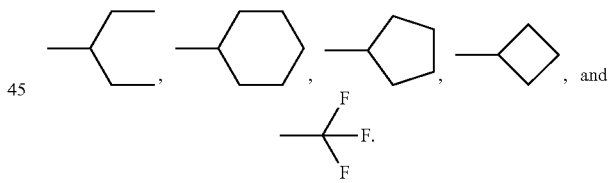

In a preferred embodiment, of this second aspect of the invention, R is selected from the group consisting of

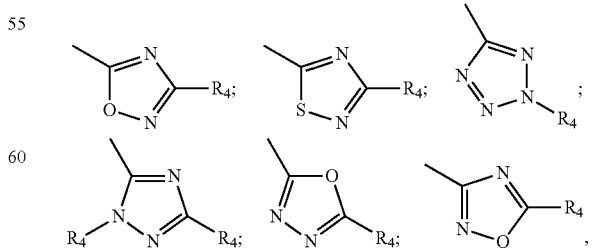

wherein R$_4$ is independently selected from the group consisting of methyl, ethyl, isopropyl, tert-butyl,

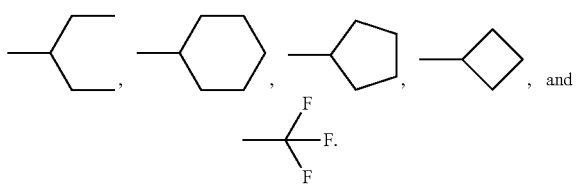

For the use of the inventive compounds as therapeutic or diagnostic agents the radiolabeled compounds may be administered to mammals, preferably humans, in a pharmaceutical composition, either alone or, preferably, in combination with one or more pharmaceutically acceptable adjuvants, excipients, carriers and diluents, according to standard pharmaceutical practice.

The precise nature of the one or more adjuvants, excipients, carriers and diluents will depend on the specific pharmaceutical dosage form comprising the pharmaceutical composition and its way of administration. However, such excipients should not unduly interfere with the biological activities of compound (I) of the radiopharmaceutical composition. A person skilled in the art will generally be able to determine and select suitable pharmaceutically acceptable excipients. Examples of pharmaceutically acceptable excipients are described in Remington's Pharmaceutical Sciences, 15$^{th}$ Ed., Mack Publishing Co., New Jersey (1991).

In particular, a preferred carrier is biocompatible and in a form suitable for mammalian, especially human, administration. Preferably, the carrier is a fluid, especially a liquid, in which the radiopharmaceutical can be dissolved, such that the composition is physiologically tolerable. More preferably, the carrier is an injectable liquid, e.g. sterile, pyrogen-free water for injection or an aqueous solution such as saline or PBS and ethanol as an adjuvant.

In a preferred embodiment, the radiopharmaceutical compositions of the invention are administered via intravenous injection within less than one hour of their synthesis in case of in-house-production; or may be distributed to external customers, preferably within 24 h.

In one embodiment, preferably in case of use in a diagnostic method, the radiopharmaceutical composition is administered preferably in an activity of about 150 to about 200 MBq, preferably about 185 MBq.

In another embodiment, preferably in case of use in a therapeutic method, the radiopharmaceutical composition is administered preferably in an individually calculated dose of up to about 40 GBq, preferably up to about 30 GBq, more preferably up to 25 GBq in case of therapy. The calculation of the maximum tolerable activity is within the knowledge of the skilled person and is performed after a dosimetry of the individual patient with about 40 MBq [$^{131}$I]-labelled radiopharmaceutical. A particular focus lies on the bone marrow which has to be as a critical organ. Postulating that the bone marrow dose does not exceed a tolerable dose of 2 Gy, high maximum tolerable activities of up to 25 GBq were calculated with the help of the computer program OLINDA.

The inventors have been shown that the compounds according to the invention are highly specific radiotracers for adrenal imaging. Further, it has been demonstrated that the compounds according to the invention bind as specifically as the compounds of the state of the art to Cyp11B enzymes which are expressed in high amounts in tissues of adrenocortical origin. Additionally, the compounds of the invention show very low background activity. Due to the improved metabolic stability the compounds of the invention offer novel diagnostic and treatment options for adrenal masses.

Therefore, in one aspect the invention provides the radiopharmaceutical composition of the invention for use in a diagnostic method for adrenal masses. Preferably, the radiopharmaceutical compound is employed in a diagnostic imaging method. In a further embodiment, the radiopharmaceutical composition is employed in single photon emission computed tomography (SPECT).

The use of the radiopharmaceutical composition of the invention in single-photon emission CT (SPECT) provides a valuable alternative to PET imaging. Furthermore, compared with PET technology the SPECT technology is more widespread in hospitals and clinics and, thus, more accessible for patients.

In a preferred embodiment, the radiopharmaceutical composition is employed in a method for differential diagnosis of adrenal masses.

Furthermore, the compounds and the radiopharmaceutical composition of the invention are particularly suitable in a method for the diagnosis of adrenocortical carcinoma.

In a further preferred embodiment, the radiopharmaceutical composition is employed in a method for the diagnosis or diagnostic imaging of a disease or disorder selected from adrenocortical carcinoma, adrenal adenoma (either endocrine active or inactive), Conn adenoma and adrenal hyperplasia in a human comprising administering to the human in need of such diagnostic imaging an effective amount of the radiopharmaceutical composition, and obtaining an image of the human. In a preferred embodiment, the image of the human is obtained using SPECT.

In another embodiment of the invention, a method of generating enhanced images of a human or animal body is provided, being previously administered with a radiopharmaceutical composition according to the invention, wherein the method comprises generating an image of at least part of said body, preferably of the adrenal area.

In another aspect of the invention, the radiopharmaceutical composition is particularly suitable in a method for the treatment of adrenocortical carcinoma in a patient by means of radionuclide therapy.

In a preferred embodiment, the radiopharmaceutical composition of the invention is intended for use in a method for the treatment of adrenocortical carcinoma. The inventive compounds are especially suitable for a targeted radionuclide therapy of advanced adrenocortical carcinoma. The high specificity of the compounds for tissues of adrenocortical origin and the improved metabolic stability of the compounds of the invention over the compounds of the state of the art allow a therapy with a higher uptake of the compound leading to extremely high levels of radioactivity in the target tissue, while the surrounding healthy tissue is largely spared. This results in good tolerability of the radiotherapy. Further, an improved therapeutic effect is provided.

For radiotherapy, the compounds or the radiopharmaceutical composition of the invention can be administered once or repeatedly, preferably within few months, e.g. from 1 to 12 months, preferably from 1 to 6 months, as appropriate for a certain patient.

In a exemplary embodiment, about thirty minutes before injection of the radiotracer, radioiodide uptake into the thyroid gland is blocked by administering a blocking agent, e.g. sodium perchlorate in an amount of about 1.15 mg orally. Thyroid blockage is generally continued for about 2 to 5 days, preferably about 3 days with an amount of about 300 to 600 mg, preferably about 400 to 500 mg, more preferably about 460 mg of sodium perchlorate 2 to 4 times, preferably 3 times daily. In case of therapy, antiemetic drugs (dimenhydrinate or ondansetrone) can be administered to the patient before administration of the compounds of the invention.

A further aspect of the invention relates to a compound having formula (I):

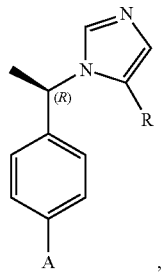
(I)

wherein A is selected from the group consisting of $^{123}$I, $^{124}$I, $^{125}$I and $^{131}$I;
R represents

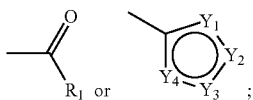

wherein $R_1$ represents

wherein each of $R_2$ and $R_3$ is independently selected from the group consisting of hydrogen and a linear or branched $C_1$-$C_4$ alkyl, optionally substituted with one or more substituents independently selected from OH, F, Cl, I and Br;
or $R_2$ and $R_3$ together form a 4-6-membered ring, optionally containing from 1 to 4 heteroatoms, selected from the group consisting of O, S, and N, optionally substituted with one or more substituents independently selected from OH, F, Cl, I and Br, a linear or branched $C_1$-$C_4$ alkyl, optionally substituted with one or more substituents independently selected from OH, F, Cl, I and Br;
each of $Y_1$, $Y_2$, $Y_3$ and $Y_4$ is independently selected from C, N, O and S,
and $Y_2$, and/or $Y_4$ is optionally substituted with a residue $R_4$ independently selected from the group consisting of hydrogen and a linear or branched $C_1$-$C_4$ alkyl, optionally substituted with one or more substituents independently selected from OH, F, Cl, I and Br;
with the proviso that $R_1$ is not pyrrolidine.
In a preferred embodiment, $R_1$ represents

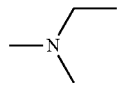

In a further preferred embodiment, $R_1$ represents

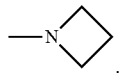

The compounds of formula (I) are radioactive labeled iodometomidate derivatives. These compounds exhibit a high specificity for tissues of adrenocortical origin and show improved metabolic stability. Therefore, the compounds of formula (I) provide for a higher uptake of the compound in the target tissue. This leads on the one hand to an improved therapeutic effect due to a higher level of radioactivity in the target tissue, while the surrounding healthy tissue is largely spared.

On the other hand, the compounds of formula (I) are highly specific radiotracers for adrenal imaging exhibiting a very low background activity. Thus, the present invention provides for an improved image quality in diagnostic methods, e.g. in diagnostic imaging of adrenal masses.

In another aspect of the invention, a method for the preparation of the radiopharmaceutical composition of the invention is provided, comprising a compound of formula (I).

The method is designed to give sterile radiopharmaceutical products suitable for human administration, e.g. via direct injection into the bloodstream.

In a method for the preparation of a compound of formula (I), preferably compounds having formula (I), wherein A represents Sn(CH$_3$)$_3$ are used as a precursor compound.

The precursor compound is reacted with radioiodide in the presence of an oxidation agent. Any suitable oxidation agent can be used and the selection of a suitable oxidation agent lies within the knowledge of a person skilled in the art. Suitable oxidation agents are chloramine-T, iodogen and peracetic acid. A preferred oxidation agent is chloramine-T.

The precursor is reacted with the oxidation agent for about 1 to about 10 minutes, preferably for about 3 to about 5 minutes.

The precursor is preferably reacted with the oxidation agent at room temperature in an acidic mixture of water and ethanol having a pH of about 1.

The reaction is quenched with a suitable agent, e.g. NaOH, a water-soluble base such as KOH or ammonium hydroxide. Preferably the reaction is quenched by addition of 1 N NaOH. The crude reaction mixture is purified by any suitable method known to a skilled person. A purification by chromatography is preferred, particularly suitable is a purification by HPLC chromatography. A suitable HPLC-system may comprise a pump, an injection system and a RP18-column and is equipped with an UV- and radioactivity detector. The HPLC-eluant is preferable a mixture of ethanol and sterile water with a pH of about 7-9.

BRIEF DESCRIPTION OF THE FIGURES

FIG. 9 shows the biodistribution of IMTO, (R)-1-[1-(4-iodophenyl)ethyl]-1H-imidazol-5-carboxylic acid azetinylamide (compound 2e), (R)-1-[1-(4-iodophenyl)ethyl]-1H-imidazol-5-carboxylic acid pyrrolidinylamid and (R)-1-[1-(4-iodophenyl)ethyl]-1H-imidazol-5-carboxylic acid ethyl-methyl amide (compound 2a) in adrenals of mice.

Figure 1:
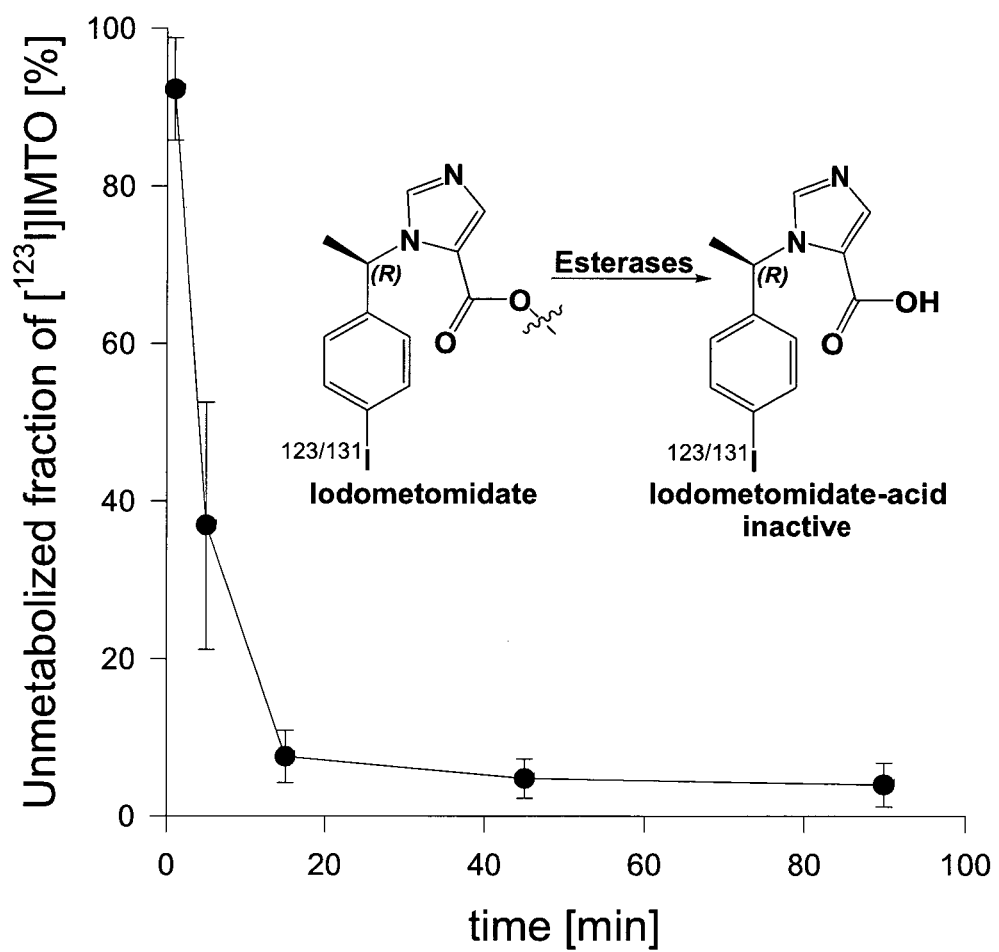
FIG. 1 shows the kinetics of IMTO metabolization.

The present invention is further illustrated by the following examples.

EXAMPLES

Example 1

1. Synthesis of the Non-Radioactive Standard 2a Via 8 Steps

Step 1: R-(+)-1-(4-Iodophenyl)-ethylamine

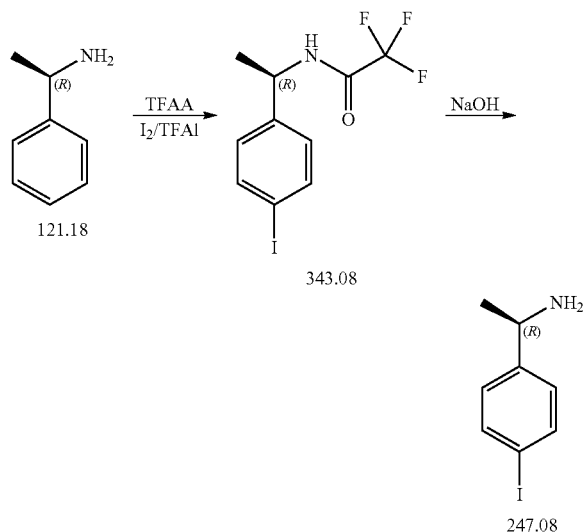

A solution of 58.6 mL (55.5 g, 458 mmol) R-(+)-1-phenylethylamine in 80 mL 1,2-dichloroethane was cooled in an ice bath, a solution of 80 mL (119 g, 570 mmol) trifluoroacetic acid anhydride in 80 mL 1,2-dichloroethane was added dropwise, and stirring was performed for 90 min at rt. After cooling in an ice bath, 55.5 g (218 mmol) iodine and 100 g (222 mmol) Bis(trifluoracetoxy)iodobenzene were added. The solution was stirred overnight and quenched by 1050 mL of a 10% sodium thiosulfate-solution. After extraction with 1000 mL methylene chloride the organic phase was washed with a saturated solution of sodium bicarbonate and dried over sodium sulfate. The solvent was stripped under reduced pressure and the crude product redissolved in 410 mL of warm diethyl ether and 113 mL hexanes. After cooling in a refrigerator, the product precipitated.

Melting point: 162-4° C.

The intermediate was dissolved in 2100 mL of methanol and 1200 mL 1 N sodium hydroxide and stirred overnight. The solution was concentrated to half of the volume under vacuum and the remaining aqueous solution was extracted with methylene chloride (4×250 mL). After drying over sodium sulfate the solvent was stripped and the product was obtained as a white solid.

Product Characteristics:

Yield 46.0 g (186 mmol, 40.6% over two steps)

Melting point: 102-8° C.

$^1$H-NMR (CDCl$_3$): δ=7.61 (d, 2H), 7.03 (d, 2H), 4.01 (q, 1H), 1.87 (bs, 2H), 1.27 (d, 3H)

Step 2: Synthesis of N-(α-Methyl-4-iodobenzyl)-glycine methylester

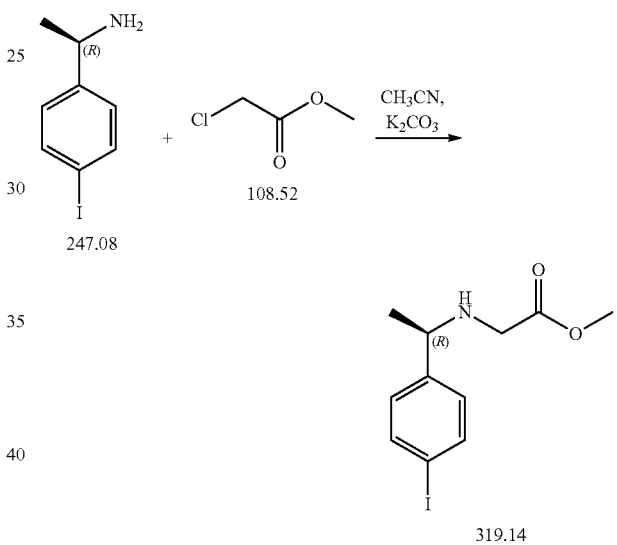

To a solution of 30 g (121 mmol) R-(+)-1-(4-iodophenyl)-ethylamine in 250 mL acetonitrile 25.0 g (201 mmol) dry potassium carbonate and 10.8 mL (13.2 g, 121 mmol) chloroacetic acid methylester were added. The solution was refluxed for 16 h under an atmosphere of argon. After cooling the solution was filtrated and the solvent stripped under vacuum. The crude product was purified by column chromatography (heptane/ethyl acetate/triethylamine 70/30/0.1).

Product Characteristics:

Yellow oil

Yield 27.4 g (85.9 mmol, 71.0%)

Thin-Layer Chromatography (Silica Gel):

R$_f$ R-(+)-1-(4-Iodophenyl)-ethylamine (heptane/ethyl acetate 80/20)=0.0

R$_f$ N-(α-Methyl-4-iodobenzyl)-glycine methylester (heptane/ethyl acetate 80/20)=0.35

$^1$H-NMR (CDCl$_3$): δ=7.62 (d, 2H), 7.12 (d, 2H), 4.20 (q, 2H), 3.81 (q, 1H), 3.38 (q, 2H), 1.94 (s, 1H), 1.43 (d, 3H), 1.29 (t, 3H)

Step 3: Synthesis of N-(α-Methyl-4-iodobenzyl)-N-formylglycine methylester

Step 5: Synthesis of N-(α-Methyl-4-iodobenzyl)-2-mercaptoimidazole-5-carboxylic acid methylester

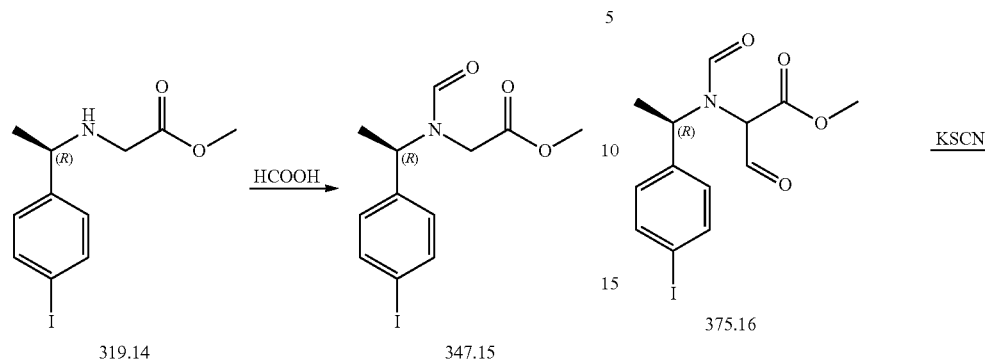

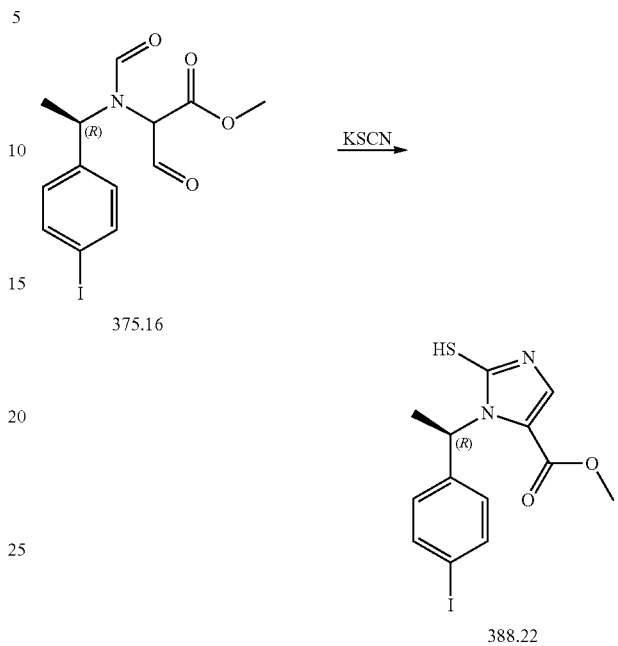

A solution of 30.0 g (94.0 mmol) N-(α-Methyl-4-iodobenzyl)-N-formylglycine methylester and 6.49 mL (7.87 g, 171 mmol) formic acid in 82 mL toluene was refluxed for 3 h. Water was removed by a dean-stark trap; the resulting solution was directly used in the next step.

Step 4: Synthesis of N-(α-Methyl-4-iodobenzyl)-N-formyl-C-formyl-glycine methylester

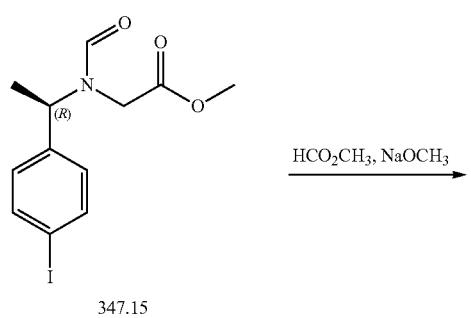

The aqueous phase obtained above was diluted with 40 mL methanol and 48 mL conc. HCl. A solution of 18.2 g (188 mmol) potassium thiocyanate in 21 mL water was added and stirring performed for 2 h at 60° C. After cooling to rt the product was extracted two times each with 82 ml tetrachloromethane and directly used in the next step.

Step 6: Synthesis of 4-Iodometomidate

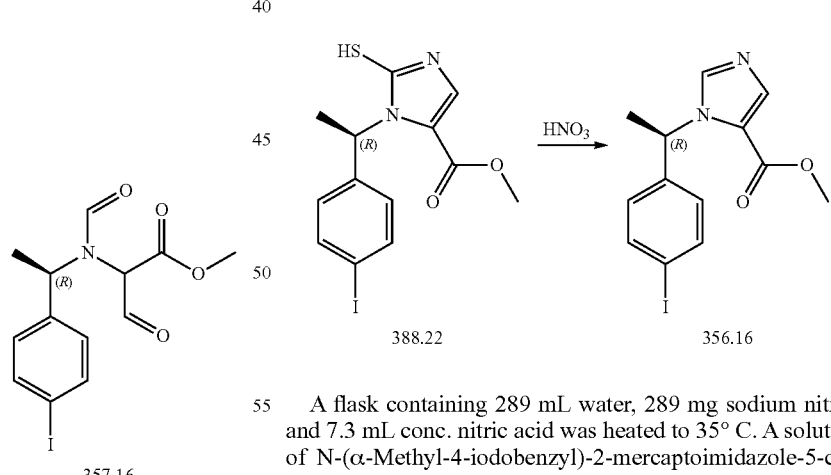

A flask containing 289 mL water, 289 mg sodium nitrite and 7.3 mL conc. nitric acid was heated to 35° C. A solution of N-(α-Methyl-4-iodobenzyl)-2-mercaptoimidazole-5-carboxylic acid methylester in 164 mL tetrachloromethane was added dropwise while the temperature was maintained below 40° C. After complete addition, the solution was stirred for 2 h at 40-50° C., cooled to rt and the phases were separated. The aqueous phase was neutralized by careful addition of sodium carbonate and the product extracted with methylene chloride. After stripping the solvents of the combined organic phases the crude product was separated by column chromatography ($CH_2Cl_2$/MeOH/DEA 97/3/0.1).

11.9 mL (11.5 g, 188 mmol) formic acid methylester and 7.66 g (141 mmol) sodium methoxide were added under cooling and stirring was performed for 16 h at rt. Finally the product was extracted as an enolate two times each with 78 mL water and directly used in the next step.

Product Characteristics:
Appearance: White solid
Melting point: 72-4° C.
Yield: 13.7 g (38.5 mmol, 40.9%)
Thin-Layer Chromatography (Silica Gel):
R$_f$ 4-Iodometomidate (heptane/ethyl acetate) (80/20)=0.10
$^1$H-NMR (CDCl$_3$): δ=9.90 (s, 1H), 8.19 (s, 1H) 7.72 (d, 2H), 7.20 (d, 2H), 6.55 (q, 1H), 3.93 (s, 3H), 2.10 (d, 3H)

Step 7: Synthesis of (R)-1-[1-(4-Iodophenyl)ethyl]-1H-imidazole-5-carboxylic acid

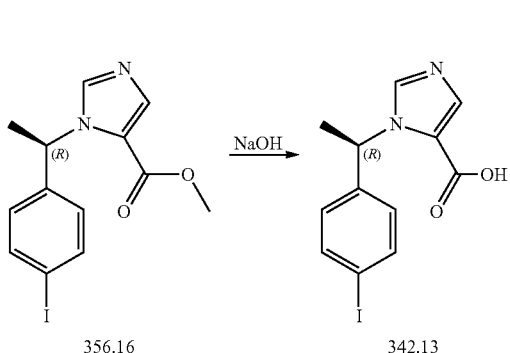

A solution of 4 g (11 mmol) Iodometomidate in 75 mL 10% NaOH was refluxed for 5 h. After cooling to rt a pH-value of 2-3 was adjusted by addition of conc. HCl. The precipitating product was filtered off and washed with water. The crude product was suspended in 100 ml toluene and dried by azeotropic distillation using a dean-stark trap. After cooling the solvent was stripped and the product was dried in a desiccator.

Product Characteristics:
Appearance: White solid
Melting point: >250° C. (dec.)
Yield: 3.32 g (9.70 mmol, 88.2%)
Thin-Layer Chromatography (Silica Gel):
R$_f$ (R)-1-[1-(4-Iodophenyl)ethyl]-1H-imidazole-5-carboxylic acid (heptane/ethyl acetate) (80/20)=0.00
$^1$H-NMR (d$_6$-DMSO): δ=8.37 (s, 1H), 7.72 (m, 3H), 6.95 (d, 2H), 6.30 (q, 1H), 1.80 (d, 3H)

Step 8: Synthesis of (R)-1-[1-(4-Iodophenyl)ethyl]-1H-imidazole-5-carboxylic acid ethylmethylamide (2a)

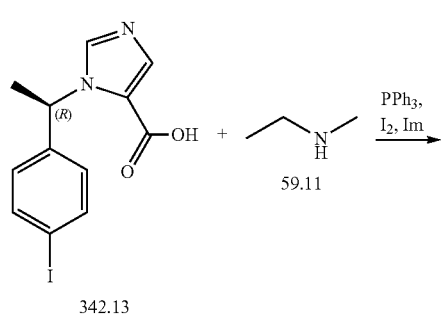

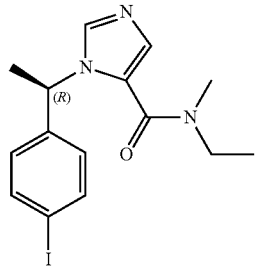

To a solution of 761 mg (3.0 mmol) iodine in 40 mL methylene chloride 787 mg (3.0 mmol) triphenylphosphine was added, giving the solution a brown-yellow color. Then, 449 mg (6.6 mmol) imidazole was added, changing the color to light yellow. Subsequently, 684 mg (2.0 mmol) (R)-1-[1-(4-iodophenyl)ethyl]-1H-imidazole-5-carboxylic acid was added and the solution was stirred for 5 min at room temperature, and 1.09 mL (740 mg, 12.5 mmol) ethylmethylamine was added and the solution stirred for two days. The solution was diluted with 50 mL chloroform, washed once with 50 mL of a saturated sodium thiosulfate-solution and three times with each 50 mL water and dried over sodium sulfate. After stripping the solvent, the crude product was purified by column chromatography (CH$_2$Cl$_2$/CH$_3$OH 95/5/).

Product Characteristics:
Appearance: Yellow oil
Yield: 293 mg (0.76 mmol, 38.2%)
Thin-Layer Chromatography (Silica Gel):
R$_f$ (R)-1-[1-(4-Iodophenyl)ethyl]-1H-imidazole-5-carboxylic acid ethylmethylamide (CH$_2$Cl$_2$/CH$_3$OH 95/5)=0.20
$^1$H-NMR (CDCl$_3$): δ=7.75 (s, 1H), 7.65 (d, 2H), 7.20 (s, 1H), 6.80 (d, 2H), 5.85 (q, 1H), 2.85 (s, 3H), 1.80 (d, 2H), 0.95 (t, 3H)

2. Synthesis of the Labelling Precursor: Synthesis of (R)-1-[1-(4-Trimethylstannyl-phenyl)ethyl]-1H-imidazole-5-carboxylic acid ethylmethylamide

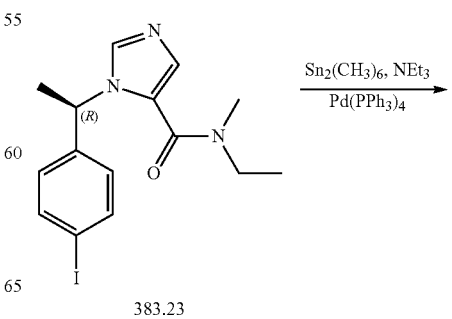

-continued

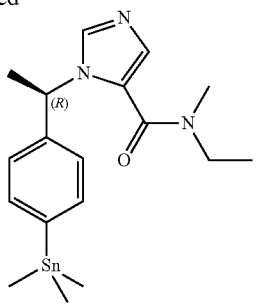

420.14

To a solution of 293 mg (0.76 mmol) (R)-1-[1-(4-iodophenyl)ethyl]-1H-imidazole-5-carboxylic acid ethylmethylamide in 12 mL toluene 728 mg (2.26 mmol) hexamethylditin, 67 mg (0.055 mmol) Tetrakis-(triphenylphosphine)-palladium (0) and 1.80 mL (1.30 g, 13.0 mmol) triethylamine were added. The solution was refluxed overnight, the solvent stripped and the crude product purified by column chromatography (100% methanol).

Product Characteristics:
Appearance: Brown-yellow oil
Yield: 206 mg (0.49 mmol, 64.5%)
Thin-Layer Chromatography (Silica Gel):
$R_f$ (R)-1-[1-(4-Trimethylstannylphenyl)ethyl]-1H-imidazole-5-carboxylic acid ethylmethylamide (heptane/EtOAc 50/50)=0.05
$^1$H-NMR (CDCl$_3$): δ=8.05 (s, 1H), 7.65 (d, 2H), 7.20 (s, 1H), 6.80 (d, 2H), 5.85 (q, 1H), 2.85 (s, 3H), 1.80 (d, 2H), 0.95 (t, 3H), 0.25 (s, 9H)

3. Radiosynthesis of [$^{131}$I](R)-1-[1-(4-Iodophenyl)ethyl]-1H-imidazole-5-carboxylic acid ethylmethylamide ([$^{131}$I]2a)

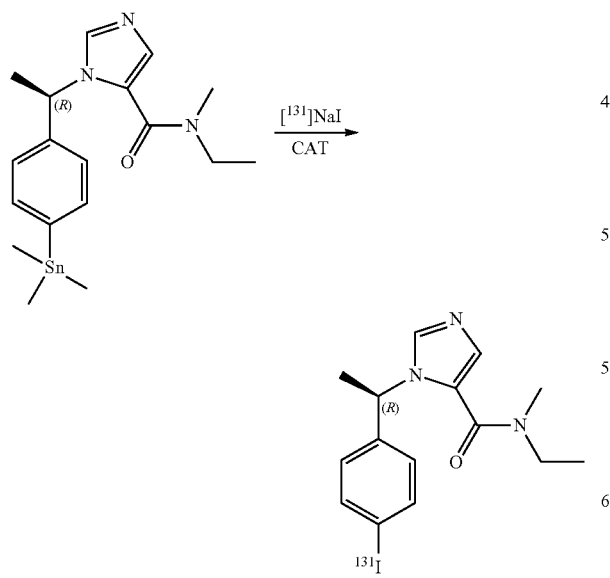

The following stock solutions were prepared:
An Eppendorf-vial containing 40 µg (R)-1-(1-(4-trimethylstannyl-phenylethyl))-1H-imidazole-5-carboxylic acid ethylmethylamide was taken from the refrigerator (−20° C.) and 30 µL ethanol were pipetted into the vial.
Oxidation agent: 15 mg Chloramin-T Trihydrate were dissolved in 10 mL water.
HPLC-eluent: methanol, water and ammonia (25%) were mixed 70/30/0.1 (v/v/v) and degassed in the ultrasonic bath.
1 N HCl
1 N NaOH To the Eppendorf-vial containing the ethanolic solution of (R)-1-(1-(4-trimethylstannyl-phenylethyl))-1H-imidazole-5-carboxylic acid ethylmethylamide a solution of sodium [$^{131}$I]iodide was pipetted. The vial was closed and the activity determined by a curiemeter. 6 µL 1 M HCl and 10 µL of the chloramin-T-solution were added and the reaction was allowed to proceed for 3 min at rt. The reaction was quenched by the addition of 7 µL 1 M NaOH. 100 µL of the HPLC-eluent were added and the solution was transferred to the HPLC-system:

Column: Nucleosil 100-7 250×4.6 mm
Eluent: Methanol/water/ammonia (25%) 70/30/0.1 (v/v/v)
Flow: 1.0 ml/min
Detection: UV (254 nm and 230 nm) and radioactivity (NaI(Tl) scintillation detector).

The HPLC-product fraction with a retention time of 7-8 min was collected in a flask and the solvent stripped under reduced pressure. The flask was transferred into a laminar airflow cabinet, the dry tracer dissolved in 3-4 mL PBS/20% ethanol and drawn into a sterile syringe. The solution was passed through a sterile filter (0.22 µm) into a sterile vial.

The tracer was obtained in a radiochemical yield of 90% and a radiochemical purity>98%.

Example 2

Synthesis of (R)-1-[1-(4-Iodophenyl)ethyl]-1H-imidazole-5-carboxylic acid azetidinylamide (2e)

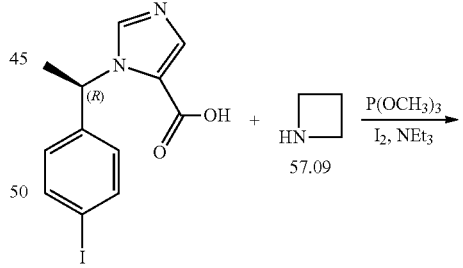

342.13

381.21

A solution of 534 µL (558 mg, 4.5 mmol) trimethylphosphite in 24 mL methylene chloride was cooled in an ice bath and was charged with 1.14 g (4.5 mmol) iodine. After complete dissolution of the iodine, 1.55 g (4.5 mmol) (R)-1-[1-(4-iodophenyl)ethyl]-1H-imidazole-5-carboxylic acid and 1.04 mL (759 mg, 7.5 mmol) triethylamine were added. 10 min later, 507 µL (429 mg, 7.5 mmol) azetidine was added and the solution stirred for 3 h at room temperature. The solution was diluted with 100 mL chloroform, washed once with 100 mL of a saturated sodium thiosulfate-solution and three times with each 50 mL water and dried over sodium sulfate. After stripping the solvent, the crude product was purified by column chromatography ($CH_2Cl_2$/$CH_3OH$ 95/5).

Product Characteristics:
Appearance: Yellow waxy solid
Yield: 770 mg (2.02 mmol, 44.9%)
Thin-Layer Chromatography (Silica Gel):
$R_f$ (R)-1-[1-(4-Iodophenyl)ethyl]-1H-imidazole-5-carboxylic acid azetidinylamide ($CH_2Cl_2$/$CH_3OH$ 95/5)=0.30
$^1$H-NMR ($CDCl_3$): δ=7.73 (s, 1H), 7.63 (d, 2H), 7.31 (s, 1H), 6.90 (d, 2H), 6.43 (q, 1H), 4.00-4.40 (m, 4H), 2.20-2.40 (m, 2H), 1.82 (d, 3H)

Step 2b: Synthesis of the Labelling Precursor

Synthesis of (R)-1-[1-(4-Trimethylstannylphenyl)ethyl]-1H-imidazole-5-carboxylic acid azetidinylamid

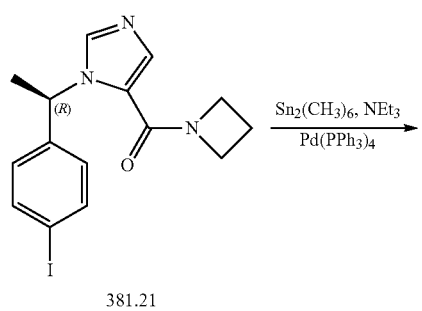

To a solution of 191 mg (0.50 mmol) (R)-1-[1-(4-iodophenyl)ethyl]-1H-imidazole-5-carboxylic acid azetidinylamide in 8 mL toluene 479 mg (1.49 mmol) hexamethylditin, 44 mg (0.036 mmol) Tetrakis-(triphenylphosphine)-palladium (0) and 1.18 mL (855 mg, 8.55 mmol) triethylamine were added. The solution was refluxed overnight, the solvent stripped and the crude product purified by column chromatography (100% ethyl acetate).

Product Characteristics:
Appearance: yellow waxy solid
Yield: 125 mg (0.30 mmol, 59.8%)
Thin-Layer Chromatography (Silica Gel):
$R_f$ (R)-1-[1-(4-Trimethylstannylphenyl)ethyl]-1H-imidazole-5-carboxylic acid ethylmethylamide ($CH_2Cl_2$/$CH_3OH$ 95/5)=0.25
$^1$H-NMR ($CDCl_3$): δ=7.72 (s, 1H), 7.43 (d, 2H), 7.25 (s, 1H), 7.19 (d, 2H), 6.43 (q, 1H), 4.00-4.35 (m, 4H), 2.20-2.35 (m, 2H), 1.82 (d, 3H), 0.28 (s, 9H)

Step 3b: Radiosynthesis of [$^{131}$I](R)-1-[1-(4-Iodophenyl)ethyl]-1H-imidazole-5-carboxylic acid azetidinylamide ([$^{131}$I]2e)

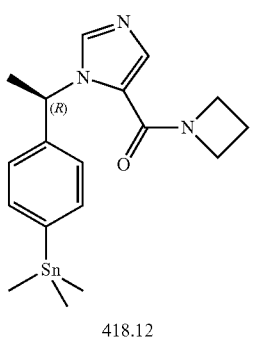

The following stock solutions were prepared:
An Eppendorf-vial containing 40 µg (R)-1-(1-(4-trimethylstannyl-phenylethyl))-1H-imidazole-5-carboxylic acid azetidinylamide was taken from the refrigerator (−20° C.) and 30 µL ethanol were pipetted into the vial.
Oxidation agent: 15 mg Chloramin-T Trihydrate were dissolved in 10 mL water.
HPLC-eluent: methanol, water and ammonia (25%) were mixed 70/30/0.1 (v/v/v) and degassed in the ultrasonic bath.
1 N HCl
1 N NaOH
To the Eppendorf-vial containing the ethanolic solution of (R)-1-(1-(4-trimethylstannyl-phenylethyl))-1H-imidazole-5-carboxylic acid ethylmethylamide a solution of sodium [$^{131}$I]iodide was pipetted. The vial was closed and the activity determined by a curiemeter. 6 µL 1 M HCl and 10 µL of the chloramin-T-solution were added and the reaction was allowed to proceed for 3 min at rt. The reaction was quenched by the addition of 7 µL 1 M NaOH. 100 µL of the HPLC-eluent were added and the solution was transferred to the HPLC-system:
Column: Nucleosil 100-7 250×4.6 mm
Eluent: Methanol/water/ammonia (25%) 70/30/0.05 (v/v/v)
Flow: 1.0 ml/min
Detection: UV (254 nm and 230 nm) and radioactivity (NaI(Tl) scintillation detector).

The HPLC-product fraction with a retention time of 8-9 min was collected in a flask and the solvent stripped under reduced pressure. The flask was transferred into a laminar airflow cabinet, the dry tracer dissolved in 3-4 mL PBS/20% ethanol and drawn into a sterile syringe. The solution was passed through a sterile filter (0.22 µm) into a sterile vial.

The tracer was obtained in a radiochemical yield of 90% and a radiochemical purity>98%.

Example 3: Evaluation of Specificity for CYB11B1 and CYP11B2 Inhibition In Vitro Plasmid constructs and transfection: To induce expression of human cytochrome P450 family 11B1 (Cyp11B1) and Cyp11B2 enzymes in Y1 cells, the full-length cDNAs for the proteins were subcloned into the multicloning site of pcDNA3.1 (zeo) (Invitrogen, Eggenstein, Germany). The cDNA fragments were isolated by PCR and digested by EcoRI. The individual fragments were ligated into the linearized vectors digested by EcoRI. Human Cyp11B1 and Cyp11B2 enzymes were expressed in Y1 cells using liposome/lipid-mediated DNA transfection. Purified plasmid DNA was mixed with Lipofectamine (Invitrogen) transfection reagents according to the manufacturer's protocol. To generate a stable Y1-Cyp11B1 and Y1-Cyp11B2 cell line, Y1 cells were transfected with the pcDNA3.1 (zeo)-Cyp11B1 and pcDNA3.1 (zeo)-Cyp11B2 vector, respectively.

Transfected cells were selected with 1000 µg/ml zeocin (Invitrogen). To screen colonies, Western blotting and real-time PCR were used to determine the level of Cyp11B1 and Cyp11B2 expression. Colonies with the highest Cyp11B expression were further tested for their ability to synthesize cortisol or aldosterone from deoxycortisol (RSS) and 11-deoxycorticosterone (DOC), respectively. Experimental protocols were standardized regarding substrate concentrations and incubation periods.

In vitro evaluation of specificity: To evaluate Cyp11B1 and Cyp11B2 inhibition by the inventive compounds, Y1-Cyp11B1 and Y1-Cyp11B2 cells were subcultured on six-well plates (0.5×106 cells per well) in 2 ml culture medium.

The enzyme reaction was started after 24 hours by the addition of 1 ml culture medium containing either 11-deoxycortisol (RSS) or 11-deoxycorticosterone (DOC) as substrate and the corresponding inhibitor. RSS and DOC were dissolved in ethanol to a final test concentration of 1 µM. For determination of $IC_{50}$ values, the inhibitors were added to the culture medium at concentrations between 0.6 nM and 60 µM and incubated for 48 h. Y1-Cyp11B1 and Y1-Cyp11B2 cells, which were treated in the same way but without inhibitors, served as controls. As further controls, untransfected Y1 cells were also incubated with RSS and DOC, respectively. Both RSS and DOC were obtained from Sigma (Deisenhofen, Germany).

The results obtained for selected compounds of the invention are presented in the following Tables 1 and 2.

TABLE 1

| compound | $R_1$ | $IC_{50}$ 11β-hydroxylase [nM] | $IC_{50}$ aldosterone synthase [nM] |
|---|---|---|---|
| iodometomidate (IMTO) | OCH$_3$ | 2.6 ± 1.1 | 2.0 ± 2.3 |
| 2a | —N(CH$_3$)(CH$_2$CH$_3$) (dimethylamino/ethyl) | 3.9 ± 0.6 | 4.2 ± 0.37 |
| 2b | —N(diethyl) | 36.6 | 10.9 ± 2.02 |
| 2e | —N(azetidinyl) | 3.16 ± 0.14 | 1.22 ± 0.08 |
| 2g | —N(piperidinyl) | 11.7 | 5.5 ± 2.2 |
| 2h | —N(morpholinyl) | 805 | 182 |

TABLE 1-continued

| compound | R₁ | IC$_{50}$ 11β-hydroxylase [nM] | IC$_{50}$ aldosterone synthase [nM] |
|---|---|---|---|
| 2i | 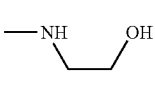 | >1000 | 15.7 |
| 2j | —NH2 | 329 ± 310 | 1410 ± 2070 |
| 2k | 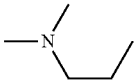 | 336 ± 398 | 221 ± 168 |
| 2l | 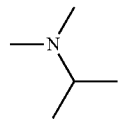 | 74.7 | 3.5 ± 7.5 |
| 2m | 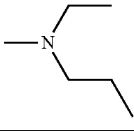 | 78.2 | 147 ± 61.9 |
| 2n | 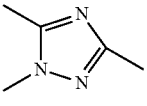 | 1322 | 390 ± 170 |

TABLE 2

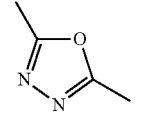

| A | R | IC$_{50}$ 11β-hydroxylase [nM] | IC$_{50}$ aldosterone synthase [nM] |
|---|---|---|---|
| 4a | | 72.6 | 1750 |
| 6a | | 10.6 ± 9.2 | 90.1 |

As can be seen from the data shown in the above table, the inventive compounds described herein bind selectively to 11β-hydroxylase and aldosterone synthase. Thus, corresponding radiopharmaceutical compositions are suitable for diagnostic and treatment purposes within the living body of a mammal having adrenal glands.

Example 4: Uptake of the Inventive Compounds in Adrenal Glands in Mice in Ex Vivo Experiments The uptake of IMTO, (R)-1-[1-(4-iodophenyl)ethyl]-1H-imidazole-5-carboxylic acid ethyl-methyl amide (compound 2a) and (R)-1-[1-(4-iodophenyl)ethyl]-1H-imidazole-5-carboxylic acid azetidinylamide (compound 2e) in adrenal glands in mice in ex vivo experiments has been examined as follows. Male CD-1 mice were injected i.v. with 1 μCi (37 kBq) IMTO, (R)-1-[1-(4-[$^{125}$I]iodophenyl)ethyl]-1H-imidazole-5-carboxylic acid ethyl-methyl amide or (R)-1-[1-(4-iodophenyl)ethyl]-1H-imidazole-5-carboxylic acid azetidinylamide (compound 2e). At predefined time points (15 min, 30 min, 120 min, and 240 min) mice were killed (n≥6 per time point) and adrenals were excised and weighed. Radioactivity was measured using a gamma-counter.

Figure 2:
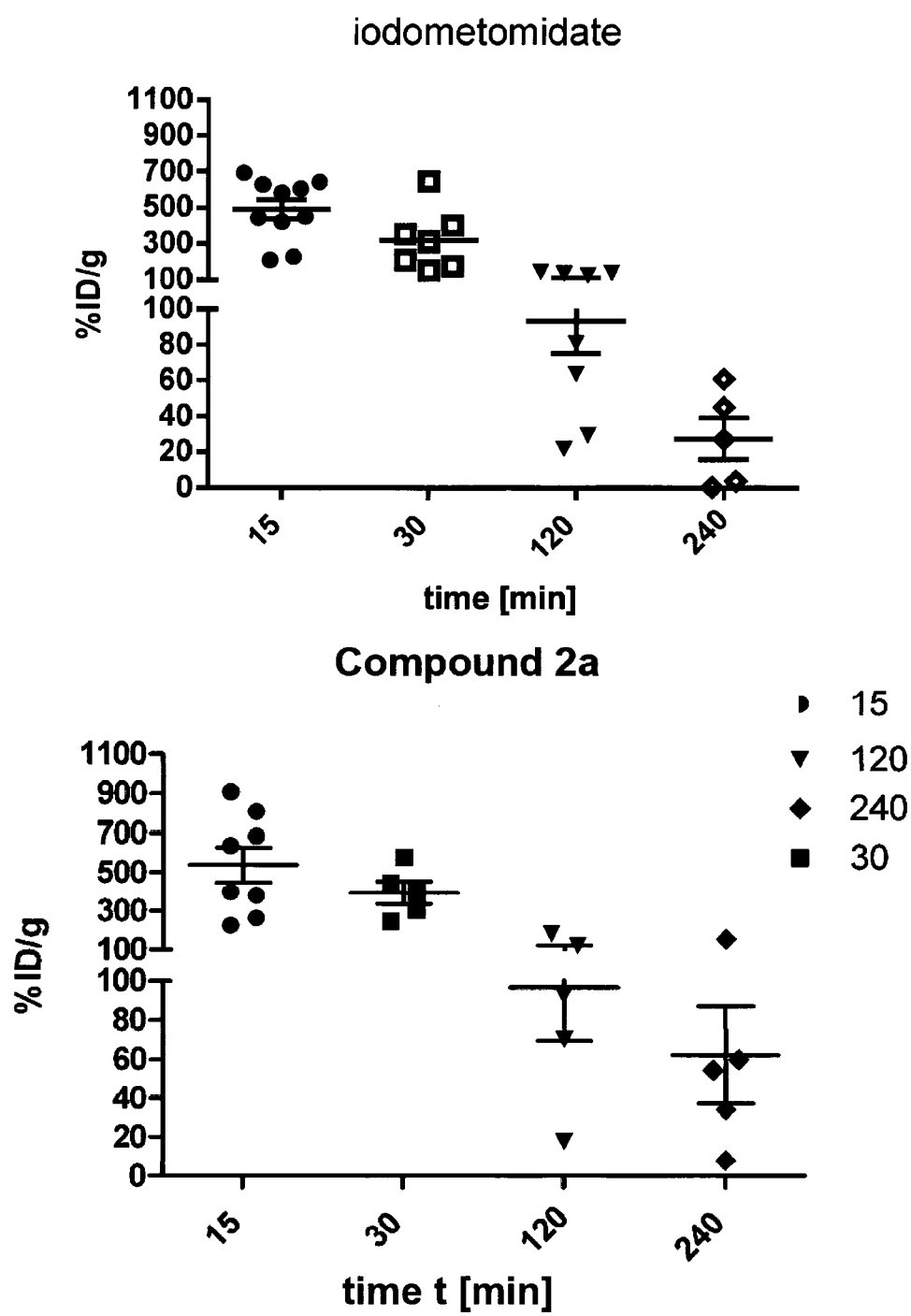
FIG. 2 shows the uptake of IMTO and (R)-1-[1-(4-iodophenyl)ethyl]-1H-imidazol-5-carboxylic acid ethylmethyl amide (compound 2a) in adrenal glands in mice in ex vivo experiments.
Figure 3:
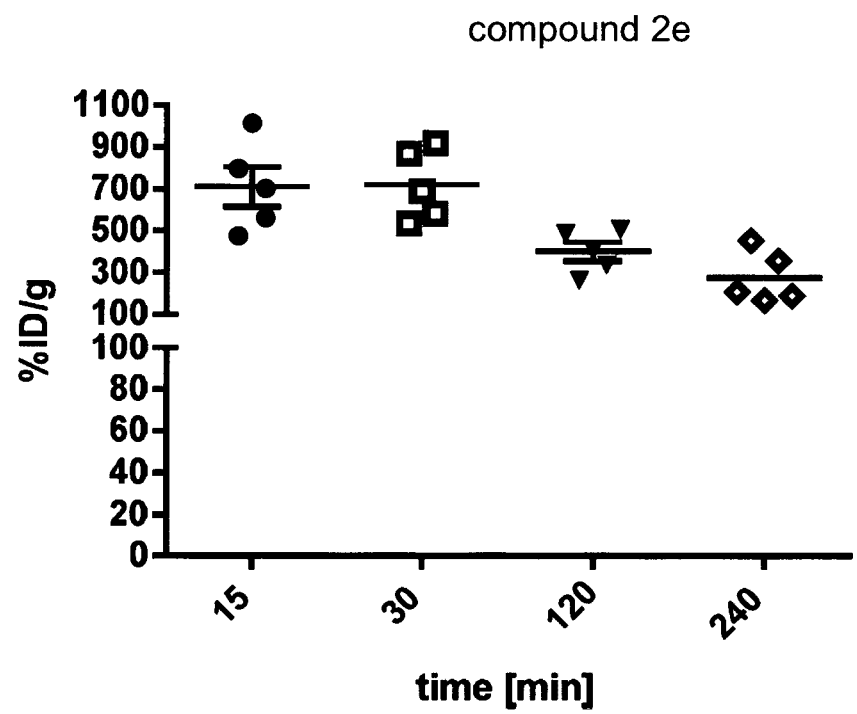
FIG. 3 shows the uptake of (R)-1-[1-(4-iodophenyl)ethyl]-1H-imidazol-5-carboxylic acid azetinylamide (compound 2e) in adrenal glands in mice in ex vivo experiments.

The results of this experiment are shown in FIGS. 2 and 3. It can be seen from the results that the uptake of compound 2a is increased compared to the state of the art compound IMTO, especially after 120 and 240 minutes. The uptake of compound 2e is greatly increased compared to IMTO at any time point. After 240 minutes the uptake is increased by a factor of about 10.

This is of great advantage, both for a diagnostic and therapeutic application of the compounds of the present invention. In diagnostic applications the higher uptake provides for an improved visualization of the target tissue. In therapeutic applications higher doses within the tumor might give improved therapeutic outcome of the patients.

Example 5: Cell Uptake Studies

Figure 4:
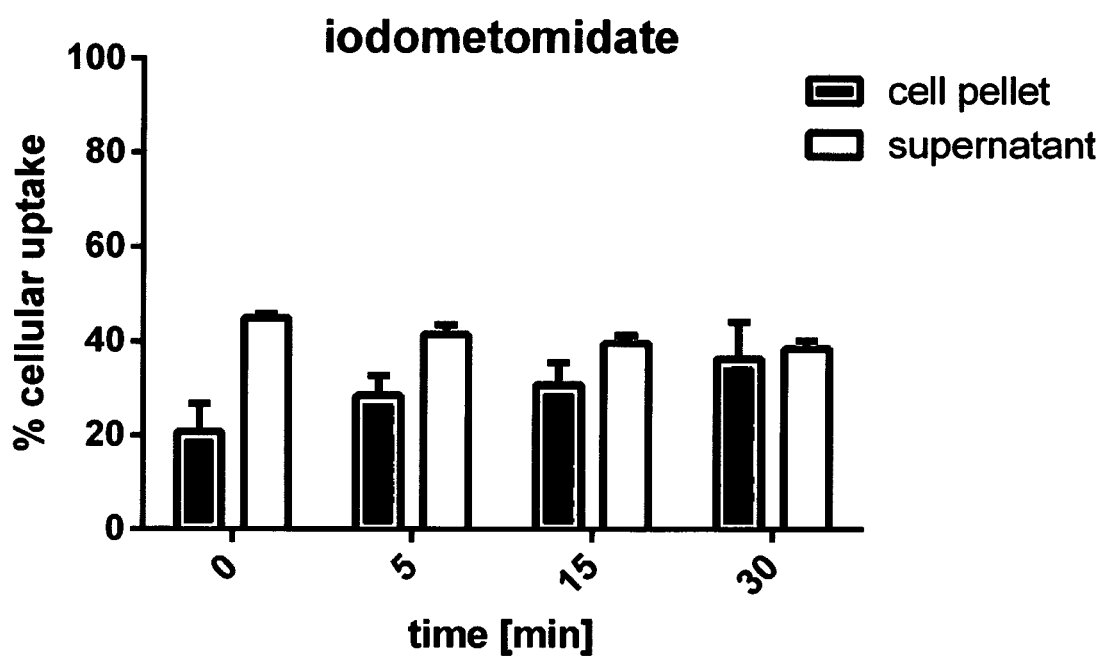
FIG. 4 shows the in vitro uptake of IMTO in cell experiments.
Figure 5:
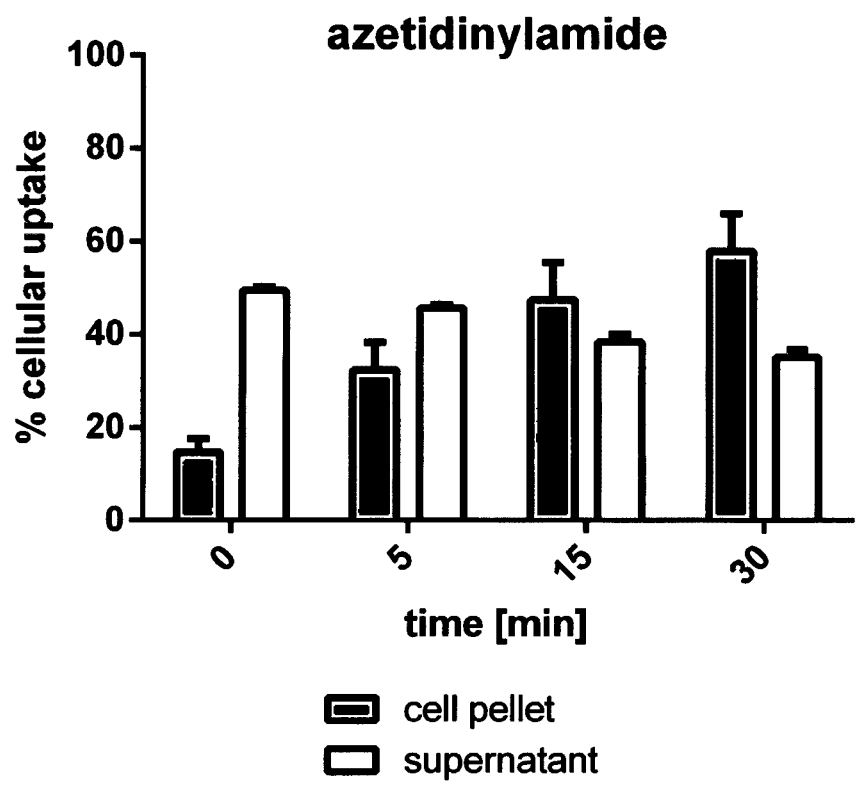
FIG. 5 shows the in vitro uptake of (R)-1-[1-(4-iodophenyl)ethyl]-1H-imidazol-5-carboxylic acid azetinylamide (compound 2e) in cell experiments.

For each experiment 250,000 NCI-H295 cells were incubated with 0.1 MBq of IMTO or (R)-1-[1-(4-iodophenyl)ethyl]-1H-imidazole-5-carboxylic acid azetidinylamide (compound 2e) at 37° C. in a humidified atmosphere (5% $CO_2$). For the blocking experiment, the cells were co-incubated with non-radioactive (0, 0.1 μM, 10 μM, 100 μM) etomidate to monitor the specific uptake of the substances. To stop the tracer uptake aliquots were taken after different time points (0 min, 2 min, 5 min, 10 min and 30 min) from the reaction mix immediately to a 4° C. ice-bath. After 5 min incubation time the solutions was centrifuged. After washing twice with PBS/0.5% Tween 80 the collected washing solution was measured in a gamma counter to determine the total amount in counts per minute (cpm) together with the samples to correct for radioactivity decay. The assay was performed in triplicates. The results of this experiment are shown in FIGS. 4 and 5.

Example 6: Biodistribution of Compound 2a in Mice

The biodistribution of IMTO, (R)-1-[1-(4-iodophenyl)ethyl]-1H-imidazole-5-carboxylic acid ethyl-methyl amide (compound 2a) and (R)-1-[1-(4-iodophenyl)ethyl]-1H-imidazole-5-carboxylic acid azetidinylamide (compound 2e) has been assessed in mice as follows. Male CD-1 mice were injected iv with 1 μCi (37 kBq) (R)-1-[1-(4-[$^{125}$I]iodophenyl)ethyl]-1H-imidazole-5-carboxylic acid ethyl-methyl amide. At predefined time points (15 min, 30 min, 2 h, and 4 h), mice were killed (n 6 per time point). Blood was collected, and heart, lung, liver, intestine, stomach, spleen, kidneys, adrenals, testes, brain and other organs were excised and weighed. Radioactivity was measured using a gamma-counter.

Figure 6:
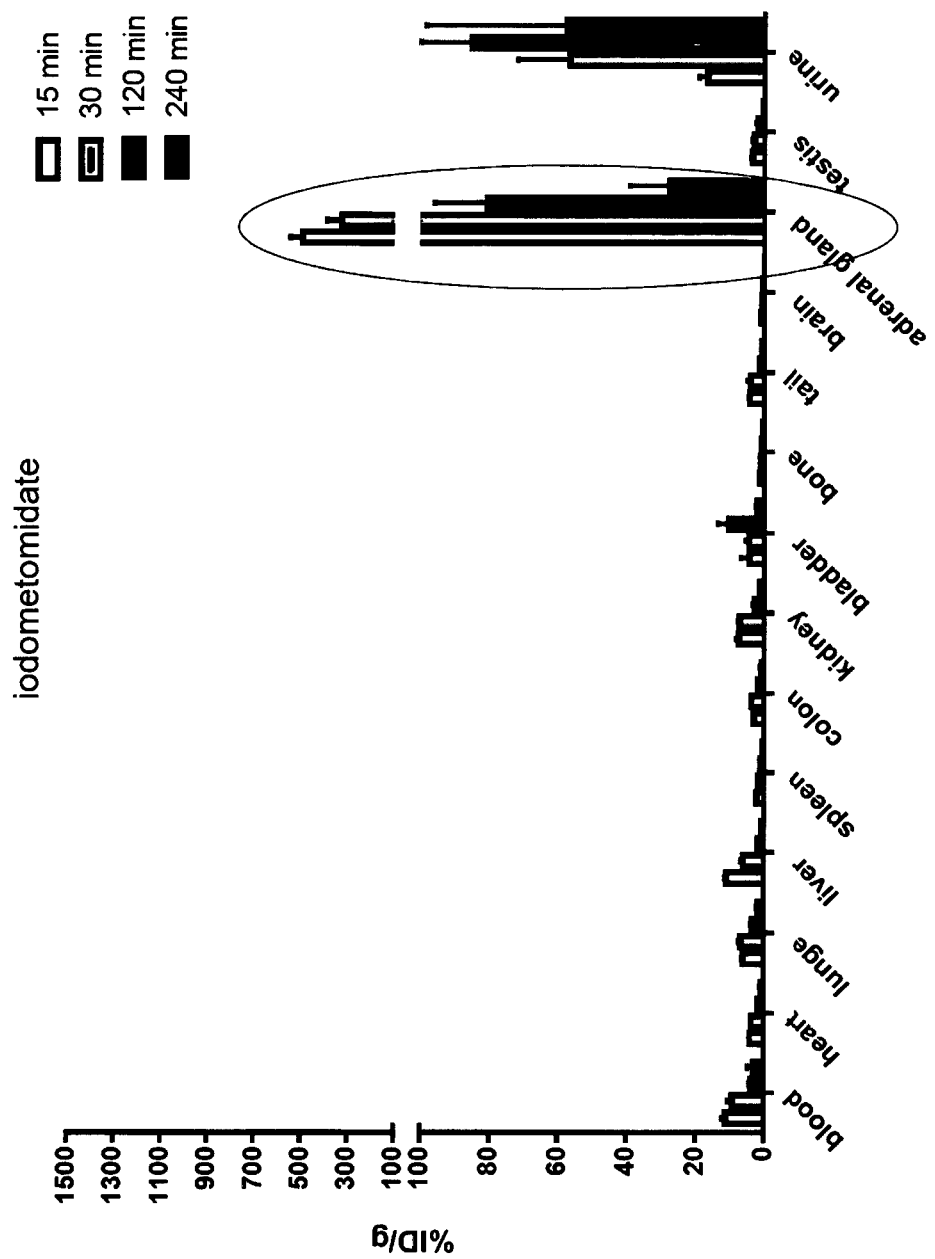
FIG. 6 shows the biodistribution of IMTO in mice.
Figure 7:
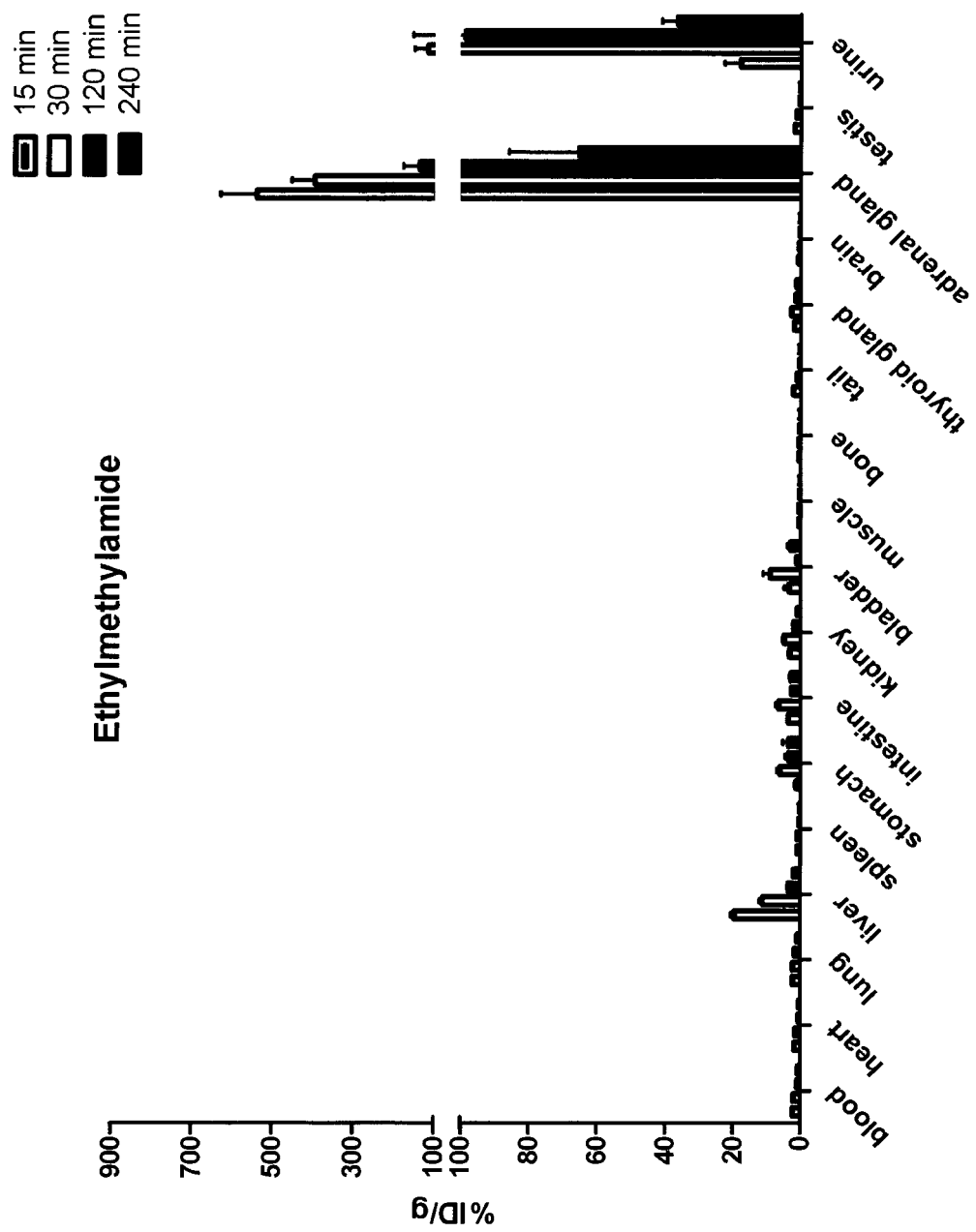
FIG. 7 shows the biodistribution of (R)-1-[1-(4-iodophenyl)ethyl]-1H-imidazol-5-carboxylic acid ethyl-methyl amide (compound 2a) in mice.
Figure 8:
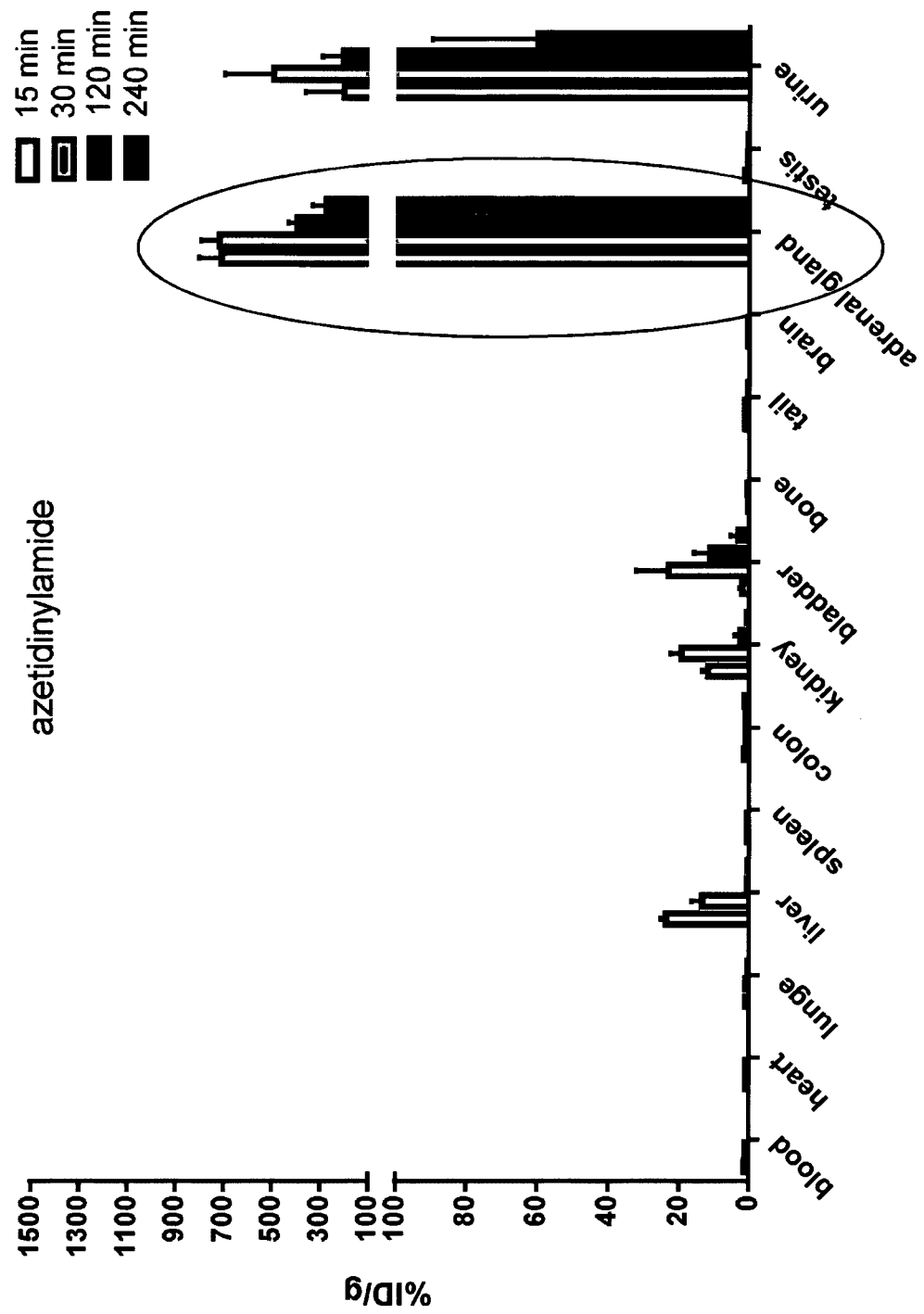
FIG. 8 shows the biodistribution of (R)-1-[1-(4-iodophenyl)ethyl]-1H-imidazol-5-carboxylic acid azetinylamide (compound 2e) in mice.

FIGS. 6-8 show the biodistribution of IMTO, (R)-1-[1-(4-iodophenyl)ethyl]-1H-imidazol-5-carboxylic acid ethyl-methyl amide (compound 2a) and (R)-1-[1-(4-iodophenyl)ethyl]-1H-imidazole-5-carboxylic acid azetidinylamide (compound 2e), respectively, in different organs and at different time points in mice. It can be seen that the uptake both of compound 2a and compound 2e is predominately in adrenal gland, i.e. that the compounds of the invention show a highly selective and specific binding.

The invention claimed is:

1. A method for the diagnosis of a Cyp11B enzyme expressing tumor comprising administering an effective amount of a radiopharmaceutical composition comprising a compound of Formula (I) to a human in need of said diagnosis, wherein Formula (I) has the structure:

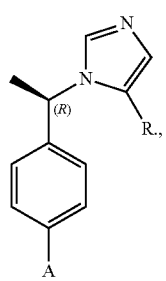

wherein A is selected from the group consisting of $^{123}$I, $^{124}$I, $^{125}$I and $^{131}$I;

R represents

wherein $R_1$ represents

and wherein $R_2$ and $R_3$ together with the N-atom, to which they are connected, form a 4-membered ring, optionally substituted with one or more substituents independently selected from the group consisting of OH, F, Cl, I, Br and a linear or branched $C_1$-$C_4$ alkyl, optionally substituted with one or more substituents independently selected from the group consisting of OH, F, Cl, I and Br;

or a pharmaceutically acceptable salt thereof, or solvate thereof.

2. A method for the diagnostic imaging of a disease or disorder comprising administering an effective amount of a radiopharmaceutical composition comprising a compound of Formula (I) to a human in need of diagnostic imaging, and obtaining an image of the human using single photon emission computed tomography, wherein Formula (I) has the structure:

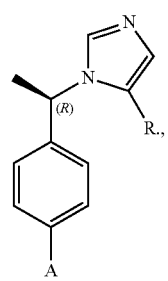

wherein A is selected from the group consisting of $^{123}$I, $^{124}$I, $^{125}$I and $^{131}$I;

R represents

wherein $R_1$ represents

and
wherein $R_2$ and $R_3$ together with the N-atom, to which they are connected, form a 4-membered ring, optionally substituted with one or more substituents independently selected from the group consisting of OH, F, Cl, I, Br and a linear or branched $C_1$-$C_4$ alkyl, optionally substituted with one or more substituents independently selected from the group consisting of OH, F, Cl, I and Br;
or a pharmaceutically acceptable salt thereof, or solvate thereof.

3. A method for treating a Cyp11B enzyme expressing tumor comprising administering an effective amount of a radiopharmaceutical composition comprising a compound of Formula (I) to a patient with the Cyp11B enzyme expressing tumor, wherein Formula (I) has the structure:

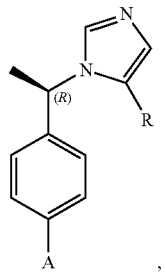

(I)

wherein A is selected from the group consisting of $^{123}$I, $^{124}$I, $^{125}$I and $^{131}$I;
R represents

wherein $R_1$ represents

and
wherein $R_2$ and $R_3$ together with the N-atom, to which they are connected, form a 4-membered ring, optionally substituted with one or more substituents independently selected from the group consisting of OH, F, Cl, I, Br and a linear or branched $C_1$-$C_4$ alkyl, optionally substituted with one or more substituents independently selected from the group consisting of OH, F, Cl, I and Br; and
or a pharmaceutically acceptable salt thereof, or solvate thereof.

4. The method of claim 2, wherein the disease or disorder is selected from the group consisting of adrenocortical carcinoma, adrenal adenoma, Conn adenoma and adrenal hyperplasia.

5. The method of claim 1, wherein the method for the diagnosis of a Cyp11B enzyme expressing tumor is by differential diagnosis.

6. The method of claim 1, wherein the Cyp11B enzyme expressing tumor is selected from an adrenal mass.

7. The method of claim 6, wherein the adrenal mass is an adrenocortical carcinoma.

8. The method of claim 1, wherein $R_1$ is selected from the group consisting of

9. The method of claim 1, wherein A is $^{131}$I.

10. The method of claim 3, wherein the Cyp11B enzyme expressing tumor is an adrenocortical carcinoma.

11. The method of claim 3, wherein $R_1$ is selected from the group consisting of

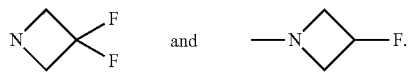

12. The method of claim 3, wherein $R_1$ represents

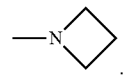

13. The method of claim 3, wherein A is $^{131}$I.

14. The method of claim 1, wherein $R_1$ represents

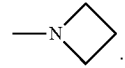

* * * * *

UNITED STATES PATENT AND TRADEMARK OFFICE
CERTIFICATE OF CORRECTION

PATENT NO. : 9,814,789 B2
APPLICATION NO. : 14/649516
DATED : November 14, 2017
INVENTOR(S) : Bruno Allolio It is certified that error appears in the above-identified patent and that said Letters Patent is hereby corrected as shown below:

In the Drawings

Drawing Sheet 6 of 9 (X-axis, Figure 6) Line 1, Change "lunge" to --lung--.

Drawing Sheet 8 of 9 (X-axis, Figure 8) Line 1, Change "lunge" to --lung--.

In the Specification

Column 11 Line 15, Change "pyrrolidinylamid" to --pyrrolidinylamide--.

Column 16 Line 35, Change "95/5/)." to --95/5).--.

Column 19 Lines 29-30, Change "azetidinylamid" to --azetidinylamide--.

In the Claims

Column 25 Lines 55-65, Claim 1, after " 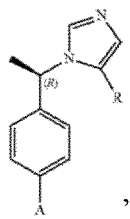 " delete ".".

Column 26 Line 26, Claim 1, change "CI," to --Cl,--.

Column 26 Line 29, Claim 1, change "CI," to --Cl,--.

Signed and Sealed this
Fourth Day of December, 2018

Andrei Iancu
*Director of the United States Patent and Trademark Office*

CERTIFICATE OF CORRECTION (continued)
U.S. Pat. No. 9,814,789 B2

Column 26 Lines 44-54, Claim 2, after " 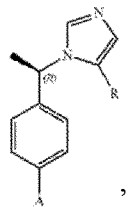 " delete ".".

Column 27 Line 13, Claim 2, change "CI," to --Cl,--.

Column 27 Line 16, Claim 2, change "CI," to --Cl,--.

Column 28 Line 5, Claim 3, change "CI," to --Cl,--.

Column 28 Line 8, Claim 3, change "CI," to --Cl,--.

Column 28 Line 9, Claim 3, after "Br;" delete "and".

Column 28 Lines 36-40, Claim 11, change "  and 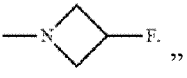 " to -- 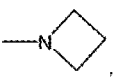 , 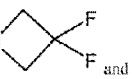 and 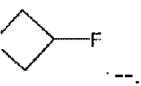 --.